(12) United States Patent
Enoch et al.

(10) Patent No.: US 11,278,733 B2
(45) Date of Patent: Mar. 22, 2022

(54) MAGNETIC EMISSION DEVICE FOR NON-INVASIVE CEREBRAL MAGNETIC STIMULATION

(71) Applicants: Université d'Aix Marseille, Marseilles (FR); Centre National de la Recherche Scientifique, Paris (FR); Ecole Centrale de Marseille, Marseilles (FR); Assistance Publique—Hôpitaux de Marseille, Marseilles (FR); Multiwave Technologies AG, Geneva (CH)

(72) Inventors: Stefan Enoch, Marseilles (FR); Redha Abdeddaim, Marseilles (FR); Éric Émile David Guedj, Marseilles (FR); Raphaëlle Richieri Le Rouzic, Marseilles (FR); Megdouda Benamara, Marseilles (FR); Marie Coralie Bultot, Aix en Provence (FR); Michael Kefeder, Geneva (CH); Tryfon Antonakakis, Geneva (CH); Elodie Georget-Paris, Geneva (CH); Fouad Fezari, Geneva (CH)

(73) Assignees: Université d'Aix Marseille, Marseilles (FR); Centre National de la Recherche Scientifique, Paris (FR); Ecole Centrale de Marseille, Marseilles (FR); Assistance Publique—Hôpitaux de Marseille, Marseilles (FR); Multiwave Technologies AG, Geneva (CH)

(*) Notice: Subject to any disclaimer, the term of this patent is extended or adjusted under 35 U.S.C. 154(b) by 0 days.

(21) Appl. No.: 17/050,342

(22) PCT Filed: Apr. 16, 2019

(86) PCT No.: PCT/FR2019/050894
§ 371 (c)(1),
(2) Date: Oct. 23, 2020

(87) PCT Pub. No.: WO2019/207236
PCT Pub. Date: Oct. 31, 2019

(65) Prior Publication Data
US 2021/0093881 A1    Apr. 1, 2021

(30) Foreign Application Priority Data
Apr. 23, 2018    (FR) .................................. 18 53549

(51) Int. Cl.
*A61N 2/02* (2006.01)
*A61N 2/00* (2006.01)

(52) U.S. Cl.
CPC ............... *A61N 2/006* (2013.01); *A61N 2/02* (2013.01)

(58) Field of Classification Search
CPC .................................. A61N 2/006; A61N 2/02
See application file for complete search history.

(56) References Cited

U.S. PATENT DOCUMENTS

| 5,496,258 | A | 3/1996 | Anninos et al. |
| 5,738,625 | A | 4/1998 | Gluck |

(Continued)

OTHER PUBLICATIONS

International Search Report dated Aug. 13, 2020 in PCT/FR2019/050894 filed on Apr. 16, 2019, 3 pages.

(Continued)

*Primary Examiner* — Christine H Matthews
(74) *Attorney, Agent, or Firm* — Oblon, McClelland, Maier & Neustadt, L.L.P.

(57) ABSTRACT

This magnetic emission device includes an antenna and further includes a device configured to select one of a plurality of predefined portions of the antenna and to connect the selected portion to a current-generating device in (Continued)

order both to cause the current to pass through the selected portion of the antenna so as to radiate a magnetic field, and to prevent the current from passing outside of the selected portion of the antenna.

20 Claims, 4 Drawing Sheets

(56) References Cited

U.S. PATENT DOCUMENTS

| | | |
|---|---|---|
| 9,782,602 B1 | 10/2017 | Lowin |
| 2009/0108969 A1 | 4/2009 | Sims et al. |
| 2010/0185042 A1 | 7/2010 | Schneider et al. |
| 2010/0286470 A1 | 11/2010 | Schneider et al. |
| 2014/0357935 A1 | 12/2014 | Ilmoniemi et al. |
| 2017/0120065 A1 | 5/2017 | Jiles et al. |
| 2017/0225004 A1 | 8/2017 | Casse et al. |
| 2017/0368366 A1 | 12/2017 | Lowin |
| 2019/0015674 A1 | 1/2019 | Lowin |

OTHER PUBLICATIONS

French Preliminary Search Report (with translation of categories) dated Feb. 7, 2019 in French Application No. 1853549 filed on Apr. 23, 2018, 4 pages.

MAGNETIC EMISSION DEVICE FOR NON-INVASIVE CEREBRAL MAGNETIC STIMULATION

The present invention relates to a magnetic emission device for non-invasive cerebral magnetic stimulation and the use of such a device.

The invention applies more specifically to a magnetic emission device for non-invasive cerebral magnetic stimulation, comprising an antenna (generally referred to as a "coil").

Non-invasive cerebral magnetic stimulation methods such as transcranial magnetic stimulation (TMS) are used to treat various neurological or psychiatric conditions such as depression, dystonia, pain, tinnitus or cerebrovascular accident sequelae (non-exhaustive list). The common principle of these methods is to non-invasively induce electric currents in regions of the brain, thus modulating their level of activity.

To induce these electric currents, the antenna is connected to an electric current-generating device so as to radiate a magnetic field in the vicinity of a human head, thereby inducing an electric current in any excitable tissue of the brain. These electric currents generate different physiological or behavioral effects according to the brain region affected and the intensity of the field.

There are antennas of different sizes and shapes, and these parameters largely determine the distribution and the penetration capacity of the magnetic field in a given brain region, the span and the spatial resolution thereof.

However, depending on the condition to be treated, it is necessary to stimulate different brain regions, and therefore to change antenna for each stimulation, which takes time and makes it necessary to have multiple different antennas available.

It may thus be desirable to provide a magnetic emission device for non-invasive cerebral magnetic stimulation that enables at least some of the problems and constraints mentioned above to be overcome.

The invention therefore relates to a magnetic emission device for non-invasive cerebral magnetic stimulation, comprising an antenna and characterized in that it further comprises means designed to select one of a plurality of predefined portions of the antenna and to connect the selected portion to a current-generating device so as both to cause the current to pass through the selected portion of the antenna in order to radiate a magnetic field and to prevent the current from passing outside of the selected portion of the antenna.

Thus, owing to the invention, it is possible to reproduce the behavior of antennas of different sizes and shapes and to offer a range of performances, simply by selecting different portions of the antenna.

Optionally, the antenna comprises at least one spiral coil having a plurality of turns and each predefined portion comprises a segment of each spiral coil.

Also optionally, the segments of each spiral coil extend, respectively, over integer numbers of turns of the spiral coil, these integer numbers being, for example, consecutive and starting, for example, with one.

Also optionally, the segments of each spiral coil extend from one and the same first point of the spiral coil to second points, respectively, spread out along the spiral coil.

Also optionally, the means comprise, for each spiral coil, a switch designed to selectively connect each of the second points to the current-generating device.

Also optionally, for each spiral coil, the first point is intended to be connected to the current-generating device.

Also optionally, for each spiral coil, the first point is located closer to the center of the spiral coil than the second points.

Also optionally, the antenna comprises two parts and the magnetic emission device further comprises a device for relative positioning of the two parts as a function of the predefined selected portion.

Also optionally, the magnetic emission device further comprises the current-generating device and the current-generating device is designed to provide a current having at least one pulse of duration between 0.5 and 4 ms, preferably between 1 and 2 ms, and of intensity between 500 and 10 000 A, preferably between 1 000 and 3 000 A.

The invention also relates to the use of a magnetic emission device according to the invention, this use comprising:
   the selection, by the means, of a first portion among the plurality of predefined portions of the antenna so that the first portion radiates a magnetic field in the head of a patient, and more generally of a subject, and
   the selection, by the means, of a second portion, different from the first, among the plurality of predefined portions of the antenna so that the second portion radiates a magnetic field in the head of the patient, and more generally of the subject.

The invention will be easier to understand in view of the following description, provided solely as an example and with reference to the appended drawings, wherein:

FIG. 1 schematically shows the general structure of a magnetic emission device for non-invasive cerebral magnetic stimulation, according to a first embodiment of the invention, FIG. 2 shows the successive steps of a method for non-invasive cerebral magnetic stimulation, according to an embodiment of the invention, FIG. 3 schematically shows the general structure of a magnetic emission device for non-invasive cerebral magnetic stimulation, according to a second embodiment of the invention, FIGS. 4, 5 and 6 show possible positionings of two spiral coils of an antenna of the magnetic emission device of FIG. 3, and FIGS. 7 to 9 are graphs showing the performance of different magnetic emission devices according to the invention, with respect to known antennas.

In reference to FIG. 1, a magnetic emission device 100 for non-invasive cerebral magnetic stimulation according to a first embodiment of the invention will now be described, as a non-limiting example.

The magnetic emission device 100 first comprises an antenna 102 comprising a flat spiral coil with straight segments having a plurality of turns (three turns in the example described) and extending from a central end S to a peripheral end $E_3$.

The magnetic emission device 100 preferably further comprises a cooling device (not shown) for the antenna 102. For example, the cooling device contains a cooling fluid (gas and/or liquid) wherein the antenna 102 is immersed. Alternatively, the antenna 102 may be hollow (tubular) and the cooling fluid flows inside the antenna 102.

The magnetic emission device 100 further comprises a current-generating device 104 designed to provide a current having at least one pulse of duration between 0.5 and 4 ms, preferably between 1 and 2 ms, and of intensity between 500 and 10 000 A, preferably between 1 000 and 3 000 A. If a pulse train is sent, this pulse train has a frequency of between 0.1 Hz and 10 kHz, preferably between 0.9 and 50 Hz. In the example described, the current-generating device 104 is connected to the central end S of the spiral coil.

The magnetic emission device 100 further comprises means 106 designed to select one of a plurality of predefined portions of the antenna 102 and to connect the selected portion to the current-generating device 104.

In the example described, each predefined portion comprises a segment of the spiral coil, extending over an integer number of spiral coil turns. Moreover, the segments extend from the same point formed, in the example described, by the central end S to points $E_1$, $E_2$, $E_3$, respectively (point $E_3$ being formed by the peripheral end $E_3$ of the spiral coil), spread out along the spiral coil from the central end S. The points S, $E_1$, $E_2$, $E_3$ are spaced apart, along the spiral coil, by substantially one spiral coil turn from one point to the next. Thus, points S and $E_1$ are spaced apart by substantially one spiral coil turn, points $E_1$ and $E_2$ are spaced apart by substantially one spiral coil turn and points $E_2$ and $E_3$ are spaced apart by substantially one spiral coil turn.

In the example described, three predefined portions of the antenna 102 are therefore provided: a first portion extending over one spiral coil turn, from point S to point $E_1$, a second portion extending over two spiral coil turns, from point S to point $E_2$, and a third portion extending over three spiral coil turns, from point S to point $E_3$ (i.e. over the entirety of the antenna 102).

To select each predefined portion, the means 106 first comprise a switch 108 designed to selectively connect each of points $E_1$, $E_2$, $E_3$ to the current-generating device 104. Thus, the current device 104 is connected between point S and the selected point $E_1$, $E_2$ or $E_3$. The current generated by the current-generating device 104 therefore passes through the selected portion of the antenna 102, but does not pass outside of this selected portion. Thus, only the selected portion of the antenna 102 radiates a magnetic field.

In the example described, the switch 108 comprises an interrupter controllable by point $E_1$, $E_2$ or $E_3$ capable of being selected, this controllable interrupter being connected both to the current-generating device and to the point $E_1$, $E_2$ or $E_3$ considered. Each controllable interrupter can be produced, for example, with transistors or electronic relays.

The means 106 further comprise a device 110 for controlling the current-generating device 104 and the switch 108. The control device 110 comprises, for example, a computer comprising a processing unit 110A and a memory 110B coupled to the processing unit 110A and intended to contain a computer program 110C comprising instructions intended to be carried out by the processing unit 110A, in order to carry out the steps implemented by the control device 110 that will be described in reference to FIG. 2. The control device 110 further comprises a human-machine interface 110D to allow control by a user.

Alternatively, all or part of the control device 110 may be formed by hardware means microprogrammed or micro-hardwired in dedicated integrated circuits. Thus, as an alternative, the control device 110 may be an electronic device comprised only of digital circuits (without a computer program) to carry out the same actions.

In reference to FIG. 2, an example of a method 200 for use of the magnetic emission device 100 in order to carry out a non-invasive cerebral magnetic stimulation will now be described.

In a step 202, the antenna 102 is placed in the vicinity of the head of a subject.

In a step 204, a user uses the interface 110D of the control device 110 to select a stimulation protocol from a plurality of predefined protocols, as well as an antenna portion from the predefined portions.

For example, the predefined protocols comprise one or more of the following protocols:
a single transcranial magnetic stimulation protocol, wherein the current-generating device 104 is controlled so as to produce a single pulse train of frequency between 0.1 Hz and 10 kHz (preferably from 0.9 Hz to 50 Hz),
paired-pulse transcranial magnetic stimulation protocol (called "paired-pulse TMS"), wherein the current-generating device 104 is controlled so as to produce two pulses separated from one another by an interval of between 1 and 500 ms,
triple/quadruple-pulse transcranial magnetic stimulation protocol (called "triple/quadruple-pulse TMS"), wherein the current-generating device 104 is controlled so as to produce three or four pulses separated from one another by an interval of between 1 ms and 5 s (preferably from 1.5 ins to 1.25 s), and
repetitive transcranial magnetic stimulation protocol (called "Repetitive TMS"), wherein the current-generating device 104 is controlled so as to produce pulses of frequency between 0.1 Hz and 10 kHz (preferably from 0.9 Hz to 50 Hz) including continuous or intermittent theta-burst stimuli.

In a step 206, the control device 110 controls the switch 108 so that the latter connects the selected antenna portion to the current-generating device 104.

In a step 208, the control device 110 controls the current-generating device 104 so that the latter provides a current according to the selected protocol.

In a step 210, the current passes through the selected portion of the antenna 102 and a magnetic field is radiated in the head of the subject. In response to the magnetic field, an electric field then appears in the head of the subject, thereby producing non-invasive cerebral magnetic stimulation.

The method then returns to step 204, in which the user can select another protocol and/or another portion of the antenna 102.

Alternatively, selection step 204 can be implemented only once for a plurality of iterations of the loop of steps 206, 208, 210. During step 204, the user then defines a sequence of protocol/portion pairs to be carried out, respectively, in each iteration of the loop of steps 206, 208, 210. For example, the following sequence can be defined: "single-pulse TMS" protocol for the first portion, then the second portion, then the third portion of the antenna 102, then "Repetitive TMS" protocol for the second portion, then for the first portion of the antenna 102. The control device 110 is then responsible for carrying out the sequence defined, without any need for the user to intervene.

In reference to FIG. 3, a magnetic emission device 300 for non-invasive cerebral magnetic stimulation according to a second embodiment of the invention will now be described, again as a non-limiting example.

The elements functionally similar to the first embodiment of FIG. 1 have the same reference numbers.

In this second embodiment, the antenna 102 has two identical spiral coils 302, 302' (it is noted that, in the context of the present invention, the term "identical" includes the case of two spiral coils that mirror one another). In the example described, the spiral coils 302, 302' each have seven turns. Moreover, the spiral coils 302, 302' respectively have central ends S, S' connected to one another and peripheral ends $E_7$, $E'_7$. They extend, furthermore, in parallel planes vertically offset (i.e. perpendicularly to these planes) with respect to one another, to allow the spiral coils 302, 302' to overlap as will be explained below.

In a manner similar to the embodiment of FIG. 1, there are a plurality of predefined portions of the antenna 102. More specifically, each predefined portion has a segment of the first spiral coil 302 and a segment of the second spiral coil 302'.

The segments of the first spiral coil 302 extend from the same point formed in the example described by the central end S to points $E_1 \ldots E_7$, respectively (point $E_7$ being formed by the peripheral end $E_7$ of the first spiral coil 302), spread out along the first spiral coil 302 from the central end S. Points S, $E_1$, $E_7$ are spaced apart, along the first spiral coil 302, by substantially one spiral coil turn from one point to the next. Thus, points S and $E_1$ are spaced apart by substantially one spiral coil turn, points $E_1$ and $E_2$ are spaced apart by substantially one spiral coil turn, and so on.

Similarly, the segments of the second spiral coil 302' extend from the same point formed in the example described by the central end S' to points $E'_1 \ldots E'_7$, respectively (point $E'_7$ being formed by the peripheral end $E'_7$ of the second spiral coil 302'), spread out along the second spiral coil 302' from the central end S'. Points S', $E'_1$, $E'_7$ are spaced apart, along the second spiral coil 302', by substantially one spiral coil turn from one point to the next. Thus, points S' and $E'_1$ are spaced apart by substantially one spiral coil turn, points $E'_1$ and $E'_2$ are spaced apart by substantially one spiral coil turn, and so on.

Below, these segments will be denoted $S-E_N$ for the first spiral coil 302 and $S'-E'_N$ for the second spiral coil 302', N varying from one to seven.

In other words, points S', $E'_1, \ldots E'_7$ are located on the second spiral coil 302' in the same way as points S, $E_1, \ldots, E_7$ are on the first spiral coil 302. Thus, each segment of the first spiral coil 302 corresponds to an identical segment of the second spiral coil 302'. For example, segment $S-E_4$ of the first spiral coil 302 and segment $S'-E'_4$ of the second spiral coil 302' are identical.

Thus, the means 106 comprise, for each spiral coil 302, 302', a switch 108, and 108' respectively, designed to selectively connect each of points $E_1$ $E_7$ of the first spiral coil 302, and each of points $E'_1 \ldots E'_7$, respectively, of the second spiral coil 302', to the current-generating device 104. The current device 104 is therefore connected between point $E_1 \ldots E_7$ selected by switch 108 and point $E'_1 \ldots E'_7$ selected by switch 108'.

So as not to overcrowd the figure, the connections between the switches 108, 108' and the points $E_1 \ldots E_7$, $E_1 \ldots E_7$ are represented by arrows starting from the switches 108, 108'.

In addition, the control device 110 is designed to control the switches 108, 108' so that each predefined portion comprises two identical segments belonging respectively to the two spiral coils 302, 302'. More specifically, points $E_1$, $E_1'$ are connected at the same time to select the first predefined portion, points $E_2$, $E_2'$ are connected at the same time to select the second predefined portion, and so on. Thus, the first predefined portion comprises both segment $S-E_1$ of the first spiral coil 302 and segment $S'-E'_1$ of the second spiral coil 302', and so on for the other predefined portions.

The magnetic emission device 300 further comprises a device 304 for relative positioning of the two spiral coils 302, 302'. For example, the positioning device 304 is designed to move the spiral coils 302, 302' in translation, one with respect to the other, in a direction parallel to the planes of the spiral coils 302, 302'.

As shown in FIG. 4, the positioning device 304 may cause the spiral coils 302, 302' to overlap.

Returning to FIG. 3, the control device 110 is further designed to control the positioning device 304 as a function of the predefined portion selected.

Two rules for the relative positioning of the spiral coils 302, 302' are provided by the control device 110.

In reference to FIG. 5, according to the first positioning rule, the spiral coils 302, 302' are positioned so that, for each spiral coil 302, 302', the point connected to the current-generating device 104 is as close as possible to the central point of the other spiral coil. FIG. 5 shows the case in which the fourth predefined portion is selected. This fourth predefined portion comprises segment $S-E_4$ and segment $S'-E'4$. Thus, the spiral coils 302, 302' are positioned so that point $E'_4$ is as close as possible to point S and point $E_4$ is as close as possible to point S'. There is an overlap of the active segments (i.e. segments of the selected predefined portion).

In reference to FIG. 6, according to the second positioning rule, the spiral coils 302, 302' are positioned so that the points connected to the current-generating device 104 of the two spiral coils are as close as possible to one another. FIG. 6 shows the case in which the fourth predefined portion is selected. This fourth predefined portion comprises segment $S-E_4$ and segment $S'-E'_4$. Thus, the spiral coils 302, 302' are positioned so that point $E'_4$ is as close as possible to point $E_4$. There is an overlap of the spiral coils, but not of the active segments (i.e. segments of the selected predefined portion). The active segments are positioned adjacent to one another.

It is noted that, in the two positioning rules illustrated in FIGS. 5 and 6, the spiral coils 302, 302' are in what is referred to as a "figure-eight antenna" position.

The magnetic emission device 300 may also be used according to the method 200 of FIG. 2.

FIG. 7 is a graph showing the performance of a magnetic emission device similar to that of FIG. 1, but using what is referred to as a circular antenna (a single circular spiral coil, for example spiral coil 302) having sixteen turns.

Each antenna is evaluated with respect to a sphere representing a head.

The ordinate of the graph indicates the depth of action, defined as the depth from the surface of the sphere at which the electric field resulting from the magnetic field of the antenna is divided by two with respect to its maximum value at the surface of the sphere. The action depth is generally referred to in the literature as "D1/2".

The abscissa of the graph indicates the action surface, defined as the ratio between the action volume and the action depth D1/2, the action volume being the volume of the sphere wherein the electric field resulting from the magnetic field of the antenna is greater than the maximum value at the surface of the sphere, divided by two. The action volume is generally referred to in the literature as "V1/2" and the action surface is generally referred to in the literature as "S1/2".

The round points indicate the performance of conventional antennas as evaluated in the article "Electric field depth-focality tradeoff in transcranial magnetic stimulation: simulation comparison of 50 coil designs" by Deng, Z. D., Lisanby, S. H., and Peterchev, A. V, published in 2013 in the journal Brain Stimulation: Basic, Translational, and Clinical Research in Neuromodulation, 6(1), 1-13. A reference of form $A_X$ is assigned to each round point, where X represents the number assigned to the antenna considered in this article.

The square points (determined by digital simulation) indicate the performance of the antenna of the invention according to the selected predefined portion. A reference of form $I_T$ is assigned to each square point, where T represents the number of turns of the selected portion. For example, reference $I_4$ corresponds to a selected portion extending (using the references used for spiral coil 302 of FIG. 3) from point S to point E4, i.e. extending over the first four turns of the spiral coil.

Figure 9:
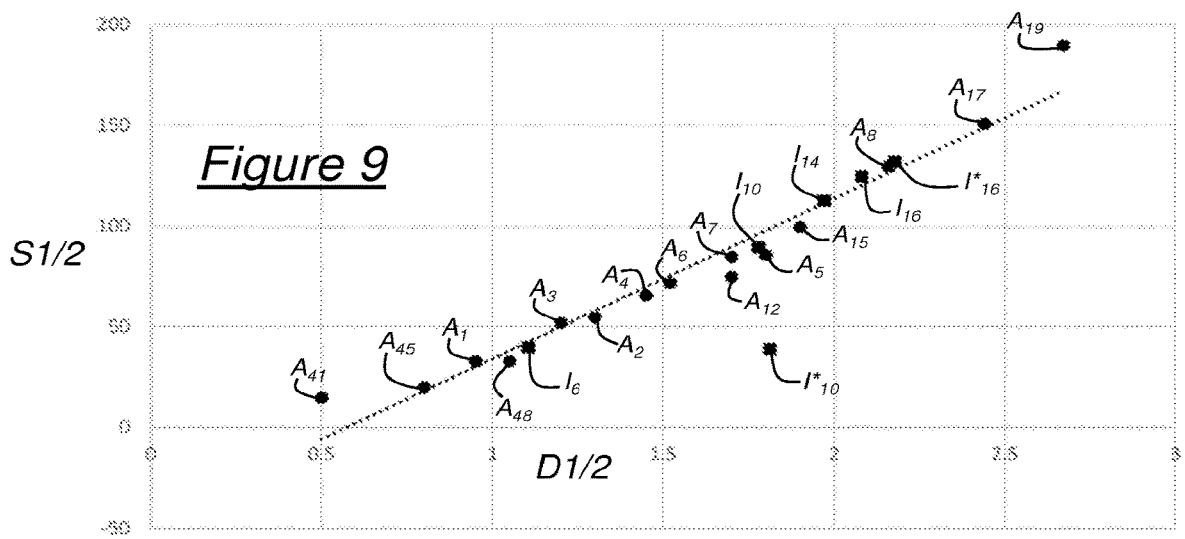
FIG. 9 is a graph similar to the graph of FIGS. 7 and 8, showing the performance of a magnetic emission device similar to that of FIG. 3, but wherein the spiral coils 302, 302' each have sixteen turns.

In FIG. 9, the references with an asterisk indicate that the second positioning rule is used (active segments overlap), while the absence of an asterisk indicates that the first positioning rule is used (active segments are adjacent).

Figure 1:
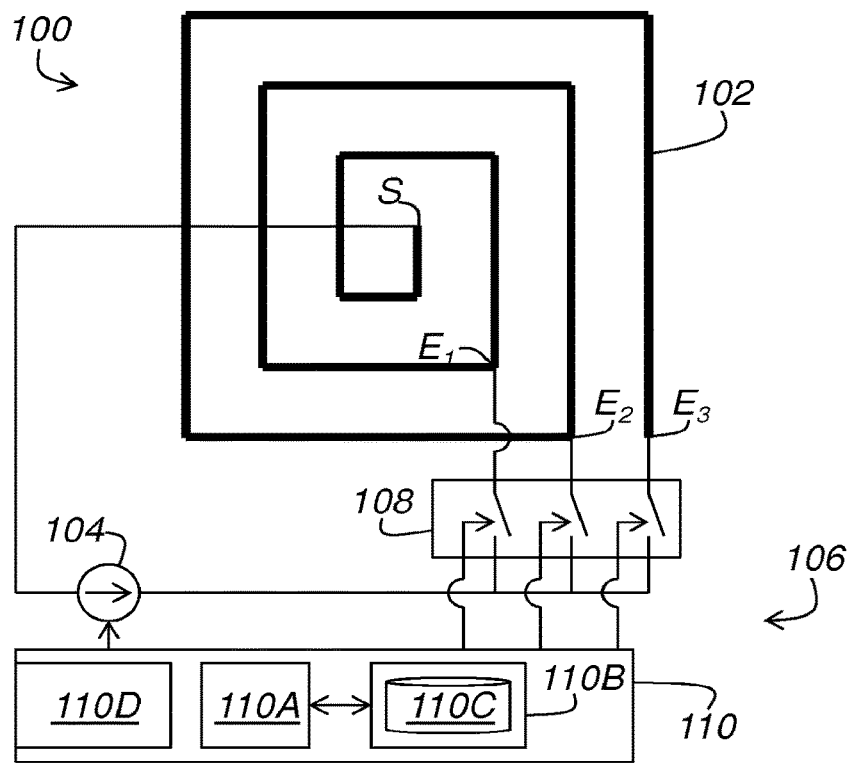
Figure 2:
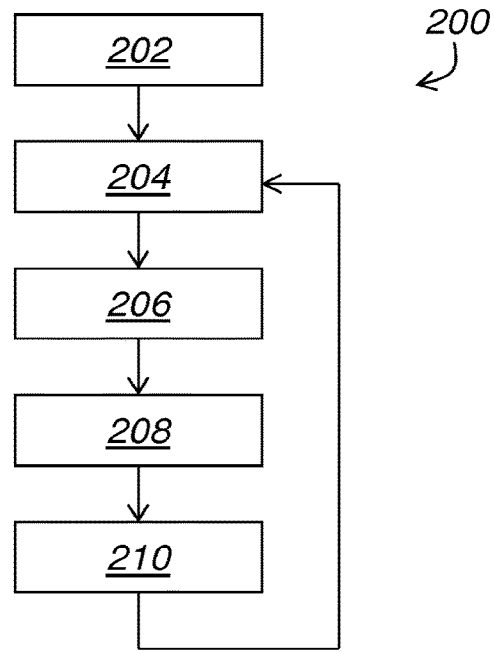
Figure 3:
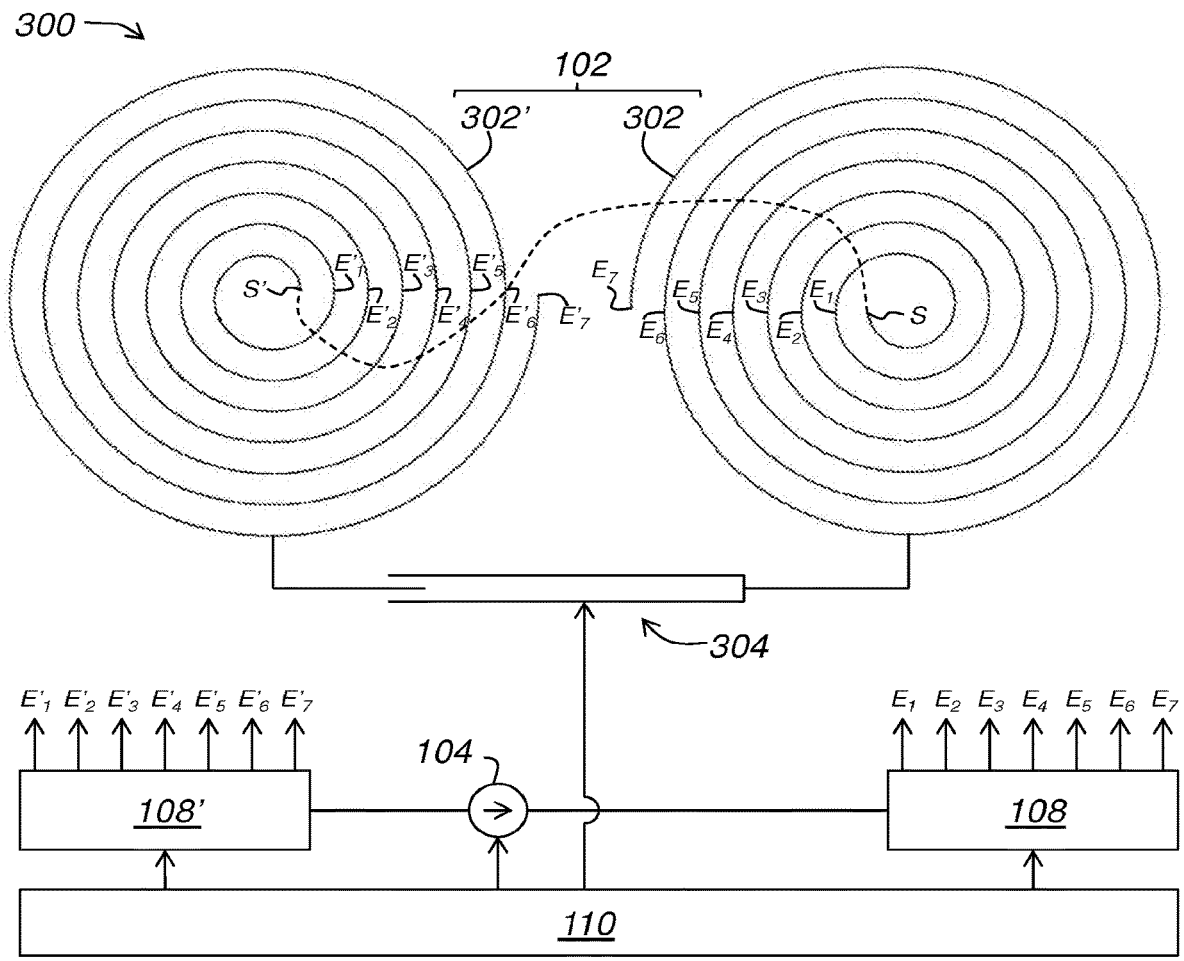
Figure 4:
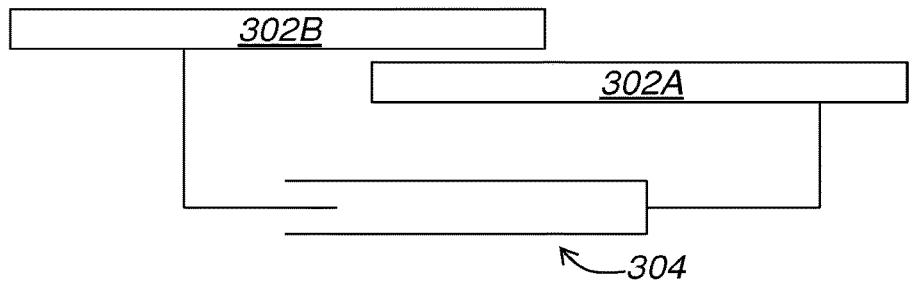
Figure 5:
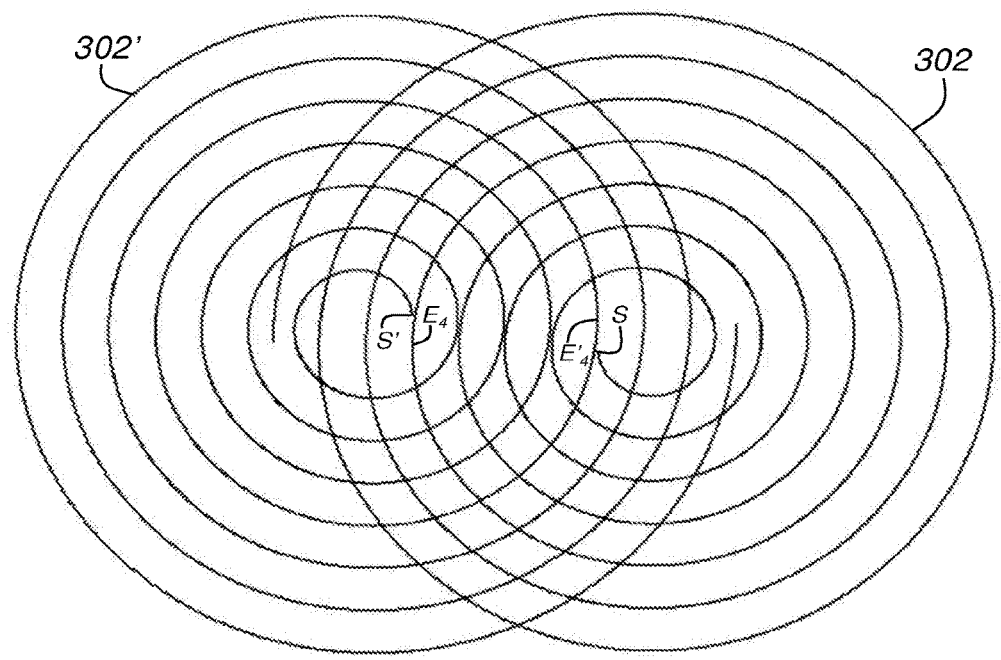
Figure 6:
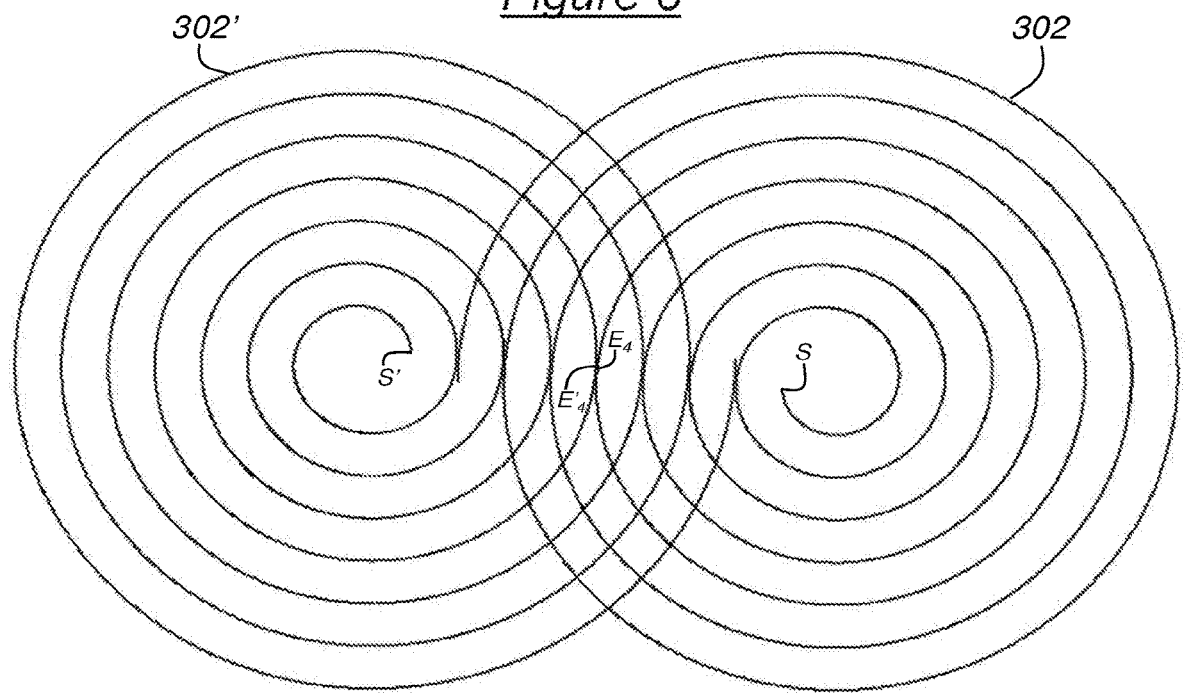
Figure 7:
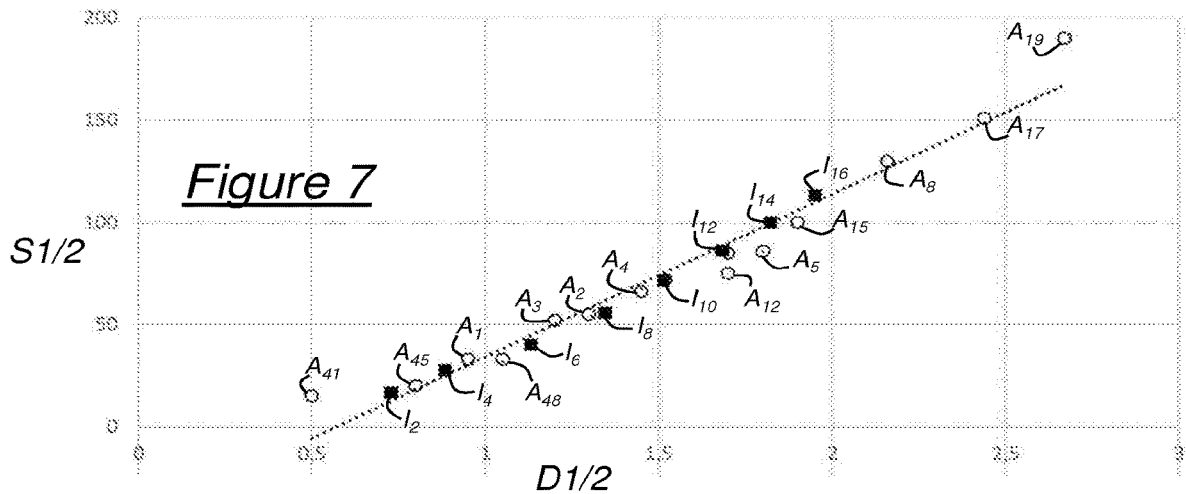
Figure 8:
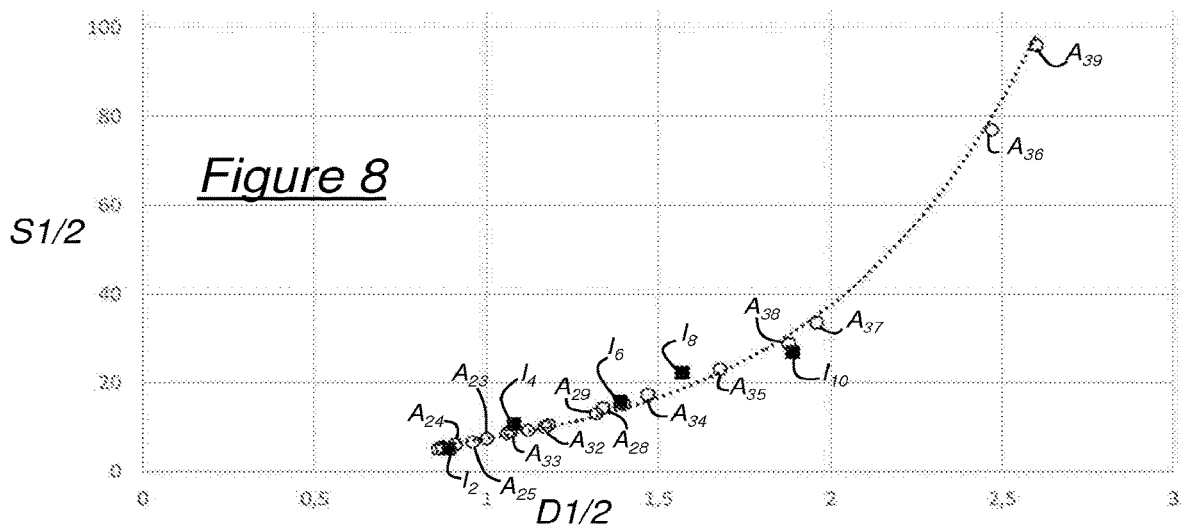
FIG. 8 is a graph similar to the graph of FIG. 7, showing the performance of a magnetic emission device similar to that of FIG. 3, but wherein the spiral coils 302, 302' each have ten turns. The second positioning rule (active segments overlap) is used.

According to FIGS. 7-9, it clearly appears that a magnetic emission device according to the invention makes it possible to effectively replace a plurality of antennas of the prior art. In particular, a careful choice of the predefined portions of the antenna makes it possible, by successively selecting carefully chosen predefined portions, to follow the same performance progression (dotted line in FIGS. 7-9) as by changing antennas of the prior art.

Moreover, a magnetic emission device according to the invention can even replace antennas of the prior art having geometries different from that of the antenna used in the magnetic emission device according to the invention. For example, the antenna used according to the invention for FIG. 7 is a circular antenna and the predefined portions are also circular antennas—only the number of turns changes. However, this makes it possible to replace, for example, the known antenna $A_8$ ("H-coil" with a particular assembly fitting in a helmet with parts according to the normal and others tangent to the skull), the known antenna $A_{15}$ (in the form of an Asian conical hat) or the known antenna $A_{41}$ (assembly of five small circular turns—two placed tangentially to the skull and three placed according to the normal to the skull and perpendicular to the first two).

It is also noted that the invention is not limited to the embodiments described above. Indeed, it will appear to a person skilled in the art that various modifications may be made to the embodiments described above, in light of the teaching that has just been disclosed. In the detailed presentation of the invention above, the terms used must not be interpreted as limiting the invention to the embodiments described in the present description, but must be interpreted as including all of the equivalents that are within reach of a person skilled in the art applying their general knowledge to the implementation of the teaching disclosed above.

The invention claimed is:

1. A magnetic emission device for non-invasive cerebral magnetic stimulation, comprising an antenna having at least one spiral coil, wherein the magnetic emission device further comprises means for selecting one of a plurality of predefined portions of the antenna, each predefined portion comprising a segment of each spiral coil, and to connect the selected portion to a current-generating device so as both to cause a current to pass through the selected portion of the antenna in order to radiate a magnetic field and to prevent the current from passing outside of the selected portion of the antenna.

2. The magnetic emission device according to claim 1, wherein each at least one spiral coil has a plurality of turns and wherein segments of each at least one spiral coil extend, respectively, over integer numbers of turns, the integer numbers being consecutive and starting at one.

3. The magnetic emission device according to claim 1, wherein the segments of each at least one spiral coil extend from a first point of the at least one spiral coil to second points, respectively, spread out along the at least one spiral coil.

4. The magnetic emission device according to claim 3, wherein the means comprises, for each at least one spiral coil, a switch configured to selectively connect each of the second points to the current-generating device.

5. The magnetic emission device according to claim 3, wherein, for each at least one spiral coil, the first point is configured to be connected to the current-generating device.

6. The magnetic emission device according to claim 3, wherein, for each at least one spiral coil, the first point is located closer to a center of the at least one spiral coil than the second points.

7. The magnetic emission device according to claim 1, wherein the antenna comprises two parts and further comprising a device for relative positioning of the two parts as a function of the predefined selected portion.

8. The magnetic emission device according to claim 1, wherein the current-generating device is configured to provide a current having at least one pulse of duration between 0.5 and 4 ms, and of intensity between 500 and 10000 A.

9. A method of using the magnetic emission device according to claim 1, comprising:
 selection, by the means, of a first portion among the plurality of predefined portions of the antenna so that the first portion radiates a magnetic field in a head of a subject, and
 selection, by the means, of a second portion, different from the first, among the plurality of predefined portions of the antenna so that the second portion radiates a magnetic field in the head of the subject.

10. The magnetic emission device according to claim 1, wherein the current-generating device is configured to provide the current having at least one pulse of duration between 1 and 2 ms.

11. The magnetic emission device according to claim 1, wherein the current-generating device is designed to provide the current having at least one pulse of intensity between 1000 and 3000 A.

12. A magnetic emission device for non-invasive cerebral magnetic stimulation, comprising:
 an antenna having at least one spiral coil, the at least one spiral coil comprising a plurality of segments;
 a current generator; and
 a switch connected to the antenna and the current generator and configured to selectively connect one of the plurality of segments to the current generator to cause a current generated by the current generator to pass through the one of the plurality of segments and not through any other ones of the plurality of segments in order to produce a first magnetic field.

13. The magnetic emission device according to claim 12, wherein the at least one spiral coil has a plurality of turns and wherein the plurality of segments of the least one spiral coil extend, respectively, over integer numbers of turns, the integer numbers being consecutive and starting at one.

14. The magnetic emission device according to claim 12, wherein the plurality of segments of the at least one spiral coil extend from a first point to second points, respectively, spread out along the at least one spiral coil.

15. The magnetic emission device according to claim 14, wherein, for each at least one spiral coil, the first point is configured to be connected to the current generator.

16. The magnetic emission device according to claim 14, wherein, for each at least one spiral coil, the first point is located closer to a center of the at least one spiral coil than the second points.

17. The magnetic emission device according to claim 12, wherein:
the antenna comprises two parts; and
the magnetic emission device comprises a device for relative positioning of the two parts.

18. The magnetic emission device according to claim 12, wherein the current generator is configured to generate a current having at least one pulse of duration between 0.5 and 4 ms, and of intensity between 500 and 10000 A.

19. The magnetic emission device according to claim 12, wherein the current generator is configured to provide at least one of:
the current having at least one pulse of duration between 1 and 2 ms, and
the current having at least one pulse of intensity between 1000 and 3000 A.

20. A method of using a magnetic emission device having an antenna having at least one spiral coil, the at least one spiral coil comprising a plurality of segments; a current generator; and a switch connected to the antenna and the current generator and configured to selectively connect one of the plurality of segments to the current generator to cause a current generated by the current generator to pass through the one of the plurality of segments and not through any other ones of the plurality of segments in order to produce a first magnetic field, the method comprising:
selecting the one segment using the switch so that the one segment radiates the first magnetic field in a head of a subject, and
selecting a second segment, different from the first segment, using the switch so that the second segment radiates a second magnetic field in the head of the subject.

* * * * *